US009463317B2

(12) United States Patent
Conroy et al.

(10) Patent No.: US 9,463,317 B2
(45) Date of Patent: Oct. 11, 2016

(54) PAIRED MEDICAL LEAD BODIES WITH BRAIDED CONDUCTIVE SHIELDS HAVING DIFFERENT PHYSICAL PARAMETER VALUES

(71) Applicant: Medtronic, Inc., Minneapolis, MN (US)

(72) Inventors: Mark J. Conroy, St. Louis Park, MN (US); Spencer M. Bondhus, Columbia Heights, MN (US); Bryan D. Stem, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/395,219

(22) PCT Filed: Jan. 29, 2013

(86) PCT No.: PCT/US2013/023637
§ 371 (c)(1),
(2) Date: Oct. 17, 2014

(87) PCT Pub. No.: WO2013/158189
PCT Pub. Date: Oct. 24, 2013

(65) Prior Publication Data
US 2015/0073518 A1 Mar. 12, 2015

Related U.S. Application Data

(60) Provisional application No. 61/635,766, filed on Apr. 19, 2012.

(51) Int. Cl.
A61N 1/08 (2006.01)
A61N 1/37 (2006.01)
A61N 1/05 (2006.01)

(52) U.S. Cl.
CPC . *A61N 1/08* (2013.01); *A61N 1/05* (2013.01); *A61N 1/3718* (2013.01); *A61N 2001/086* (2013.01)

(58) Field of Classification Search
CPC ................ A61N 1/05–1/06; A61N 2001/086; A61B 5/04286
See application file for complete search history.

(56) References Cited

U.S. PATENT DOCUMENTS 2,433,480 A 12/1947 Rendich
2,487,038 A 11/1949 Jasper
(Continued)

FOREIGN PATENT DOCUMENTS

EP 0617978 10/1994
EP 0624383 11/1994
(Continued)

OTHER PUBLICATIONS

PCT/US2004/042081: Search Report and Written Opinion.
(Continued)

*Primary Examiner* — Eugene Wu
(74) *Attorney, Agent, or Firm* — Withers & Keys, LLC

(57) ABSTRACT

Medical lead bodies that are paired each include a braided conductive shield. The braided conductive shield of one lead body has a value for a physical parameter that differs from a value for the physical parameter of the second lead body. The difference in values of the physical parameter for the paired lead bodies results in a reduction in heating from exposure of the lead bodies to radiofrequency energy at electrodes associated with the lead bodies. The lead bodies may be paired by being implanted adjacently to one another. The lead bodies may be further paired by being coupled to a same distal body, such as a paddle containing the electrodes.

26 Claims, 10 Drawing Sheets

(56) References Cited

U.S. PATENT DOCUMENTS

| | | |
|---|---|---|
| 3,788,329 A | 1/1974 | Friedman |
| 3,842,485 A | 10/1974 | Bement |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,332,259 A * | 6/1982 | McCorkle, Jr. .......... A61N 1/056 607/123 |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakeley et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,491,299 A * | 2/1996 | Naylor .............. A61B 5/04286 174/105 R |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 5,995,861 A * | 11/1999 | Price .................. A61B 5/04085 600/372 |
| 6,004,269 A | 12/1999 | Crowley |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,066,165 A * | 5/2000 | Racz .................. A61N 1/0553 607/117 |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |

(56) References Cited

U.S. PATENT DOCUMENTS

| | | | |
|---|---|---|---|
| 6,587,733 B1 * | 7/2003 | Cross, Jr. | A61B 5/04001 600/393 |
| 6,606,521 B2 | 8/2003 | Paspa et al. | |
| 6,640,137 B2 | 10/2003 | MacDonald | |
| 6,648,690 B2 | 11/2003 | Saito et al. | |
| 6,660,116 B2 | 12/2003 | Wolf et al. | |
| 6,671,544 B2 | 12/2003 | Baudino | |
| 6,671,554 B2 | 12/2003 | Gibson et al. | |
| 6,673,999 B1 | 1/2004 | Wang et al. | |
| 6,675,033 B1 | 1/2004 | Lardo et al. | |
| 6,689,835 B2 | 2/2004 | Amarasekera et al. | |
| 6,695,761 B2 | 2/2004 | Oschman et al. | |
| 6,708,051 B1 | 3/2004 | Durousseau | |
| 6,711,440 B2 | 3/2004 | Deal et al. | |
| 6,712,844 B2 | 3/2004 | Pacetti et al. | |
| 6,713,671 B1 | 3/2004 | Wang et al. | |
| 6,718,203 B2 | 4/2004 | Weiner et al. | |
| 6,718,207 B2 | 4/2004 | Connelly | |
| 6,725,092 B2 | 4/2004 | MacDonald et al. | |
| 6,735,471 B2 | 5/2004 | Hill et al. | |
| 6,741,892 B1 | 5/2004 | Meadows et al. | |
| 6,743,055 B1 | 6/2004 | Flynn | |
| 6,750,055 B1 | 6/2004 | Connelly et al. | |
| 6,757,566 B2 | 6/2004 | Weiner et al. | |
| 6,760,628 B2 | 7/2004 | Weiner et al. | |
| 6,763,268 B2 | 7/2004 | MacDonald et al. | |
| 6,765,144 B1 | 7/2004 | Wang et al. | |
| 6,768,053 B1 | 7/2004 | Wang et al. | |
| 6,778,856 B2 | 8/2004 | Connelly et al. | |
| 6,792,316 B2 | 9/2004 | Sass | |
| 6,793,642 B2 | 9/2004 | Connelly et al. | |
| 6,795,730 B2 | 9/2004 | Connelly et al. | |
| 6,795,736 B2 | 9/2004 | Connelly et al. | |
| 6,799,067 B2 | 9/2004 | Pacetti | |
| 6,799,069 B2 | 9/2004 | Weiner et al. | |
| 6,815,609 B1 | 11/2004 | Wang et al. | |
| 6,819,954 B2 | 11/2004 | Connelly | |
| 6,819,958 B2 | 11/2004 | Weiner et al. | |
| 6,844,492 B1 | 1/2005 | Wang et al. | |
| 6,845,259 B2 | 1/2005 | Pacetti et al. | |
| 6,845,267 B2 | 1/2005 | Harrison et al. | |
| 6,846,985 B2 | 1/2005 | Wang et al. | |
| 6,850,805 B2 | 2/2005 | Connelly et al. | |
| 6,852,091 B2 | 2/2005 | Edwards et al. | |
| 6,863,653 B1 | 3/2005 | Zanelli et al. | |
| 6,864,418 B2 | 3/2005 | Wang et al. | |
| 6,869,683 B2 | 3/2005 | Sakurai et al. | |
| 6,871,091 B2 | 3/2005 | Wilkinson et al. | |
| 6,872,882 B2 | 3/2005 | Fritz | |
| 6,875,180 B2 | 4/2005 | Weiner et al. | |
| 6,879,861 B2 | 4/2005 | Benz et al. | |
| 6,882,519 B2 | 4/2005 | Uzawa et al. | |
| 6,895,280 B2 | 5/2005 | Meadows et al. | |
| 6,901,287 B2 | 5/2005 | Davis et al. | |
| 6,901,290 B2 | 5/2005 | Foster et al. | |
| 6,906,256 B1 | 6/2005 | Wang | |
| 6,920,361 B2 | 7/2005 | Williams | |
| 6,922,590 B1 | 7/2005 | Whitehurst | |
| 6,925,328 B2 | 8/2005 | Foster et al. | |
| 6,930,242 B1 | 8/2005 | Helfer | |
| 6,937,906 B2 | 8/2005 | Terry et al. | |
| 6,944,489 B2 | 9/2005 | Zeijlemaker et al. | |
| 6,949,929 B2 | 9/2005 | Gray et al. | |
| 6,954,674 B2 | 10/2005 | Connelly | |
| 6,968,235 B2 | 11/2005 | Belden et al. | |
| 6,968,236 B2 | 11/2005 | Hagele | |
| 6,971,391 B1 | 12/2005 | Wang et al. | |
| 6,980,865 B1 | 12/2005 | Wang et al. | |
| 6,982,378 B2 | 1/2006 | Dickson | |
| 6,985,775 B2 | 1/2006 | Reinke et al. | |
| 6,993,387 B2 | 1/2006 | Connelly et al. | |
| 6,999,818 B2 | 2/2006 | Stevenson et al. | |
| 6,999,821 B2 | 2/2006 | Jenney et al. | |
| 7,001,369 B2 | 2/2006 | Griffin et al. | |
| 7,013,174 B2 | 3/2006 | Connelly et al. | |
| 7,013,180 B2 | 3/2006 | Villaseca et al. | |
| 7,015,392 B1 | 3/2006 | Dickenson | |
| 7,015,393 B2 | 3/2006 | Weiner | |
| 7,047,084 B2 | 5/2006 | Erickson | |
| 7,050,855 B2 | 5/2006 | Zeijlemaker et al. | |
| 7,058,192 B2 | 6/2006 | Muller et al. | |
| 7,076,283 B2 | 7/2006 | Cho et al. | |
| 7,076,302 B2 | 7/2006 | Scheiner | |
| 7,082,328 B2 | 7/2006 | Funke | |
| 7,082,337 B2 | 7/2006 | Sommer et al. | |
| 7,103,413 B2 | 9/2006 | Swanson | |
| 7,113,827 B2 | 9/2006 | Silvestri | |
| 7,115,134 B2 | 10/2006 | Chambers | |
| 7,118,693 B2 | 10/2006 | Glatkowski et al. | |
| 7,123,013 B2 | 10/2006 | Gray | |
| 7,125,409 B2 | 10/2006 | Truckai et al. | |
| 7,162,302 B2 | 1/2007 | Wang et al. | |
| 7,174,219 B2 | 2/2007 | Wahlstrand et al. | |
| 7,187,980 B2 | 3/2007 | Osypka et al. | |
| 7,233,825 B2 | 6/2007 | Jorgenson et al. | |
| 7,257,449 B2 | 8/2007 | Bodner | |
| 7,282,260 B2 | 10/2007 | LeGrande et al. | |
| 7,286,871 B2 | 10/2007 | Cohen | |
| 7,286,882 B2 | 10/2007 | Cole | |
| 7,292,894 B2 | 11/2007 | Belden | |
| 7,294,785 B2 * | 11/2007 | Uutela | A61B 5/04286 174/74 R |
| 7,319,901 B2 | 1/2008 | Dublin | |
| 7,363,090 B2 | 4/2008 | Halperin | |
| 7,389,148 B1 | 6/2008 | Morgan | |
| 7,540,865 B2 | 6/2009 | Griffin et al. | |
| 7,548,788 B2 | 6/2009 | Chinn et al. | |
| 7,591,831 B2 | 9/2009 | Parsonage et al. | |
| 7,674,972 B2 | 3/2010 | Gladd et al. | |
| 7,711,436 B2 | 5/2010 | Stone | |
| 7,729,777 B2 | 6/2010 | Gray et al. | |
| 7,738,942 B2 | 6/2010 | Weiner | |
| 7,813,811 B2 | 10/2010 | Wingeier et al. | |
| 7,819,826 B2 | 10/2010 | Diederich et al. | |
| 7,822,484 B1 | 10/2010 | Zhao et al. | |
| 7,828,833 B2 | 11/2010 | Haverkost | |
| 7,844,343 B2 | 11/2010 | Wahlstrand | |
| 7,844,344 B2 | 11/2010 | Wahlstrand | |
| 7,853,332 B2 | 12/2010 | Olsen | |
| 7,877,150 B2 * | 1/2011 | Hoegh | A61N 1/0534 607/119 |
| 7,904,178 B2 | 3/2011 | Williams | |
| 7,917,213 B2 | 3/2011 | Bulkes | |
| 7,933,652 B2 | 4/2011 | Phillips | |
| 8,007,440 B2 | 8/2011 | Magnin et al. | |
| 8,027,736 B2 | 9/2011 | Wahlstrand | |
| 8,036,756 B2 | 10/2011 | Swoyer et al. | |
| 8,048,060 B2 | 11/2011 | Griffin et al. | |
| 8,055,351 B2 | 11/2011 | Atalar et al. | |
| 8,106,657 B2 | 1/2012 | Sakellariou et al. | |
| 8,170,691 B2 | 5/2012 | Eckerdal | |
| 8,202,259 B2 | 6/2012 | Evans et al. | |
| 8,246,643 B2 | 8/2012 | Nita | |
| 8,275,464 B2 | 9/2012 | Li et al. | |
| 8,280,526 B2 | 10/2012 | Wahlstrand | |
| 8,483,842 B2 | 7/2013 | Alexander et al. | |
| 8,620,455 B2 | 12/2013 | Alexander et al. | |
| 8,666,513 B2 * | 3/2014 | Ameri | A61N 1/05 607/119 |
| 8,676,340 B2 | 3/2014 | Wahlstrand | |
| 8,744,598 B2 | 6/2014 | Alexander et al. | |
| 8,788,061 B2 | 7/2014 | Mehdizadeh | |
| 8,805,534 B2 | 8/2014 | Olsen | |
| 8,903,504 B2 | 12/2014 | Hegland | |
| 9,002,474 B2 | 4/2015 | Olsen | |
| 9,037,263 B2 | 5/2015 | Marshall | |
| 9,044,593 B2 | 6/2015 | Li | |
| 2001/0044646 A1 | 11/2001 | Marshall et al. | |
| 2002/0032468 A1 | 3/2002 | Hill | |
| 2002/0038135 A1 | 3/2002 | Connelly et al. | |
| 2002/0058978 A1 | 5/2002 | Sass | |
| 2002/0082673 A1 | 6/2002 | Benz et al. | |
| 2002/0106918 A1 | 8/2002 | Saito et al. | |
| 2002/0111659 A1 | 8/2002 | Davis et al. | |

(56) References Cited

U.S. PATENT DOCUMENTS

| | | |
|---|---|---|
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183438 A1 | 12/2002 | Amarasekera et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0204228 A1* | 10/2003 | Cross, Jr. ............ A61N 1/0553 607/116 |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0004639 A1* | 1/2005 | Erickson ............ A61N 1/0529 607/122 |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Femano et al. |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0255373 A1* | 11/2007 | Metzler ............... A61N 1/0553 607/117 |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0249390 A1* | 10/2008 | McIntire ............. A61B 5/0006 600/372 |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0069743 A1 | 3/2010 | Sheetz et al. |
| 2010/0070010 A1* | 3/2010 | Simpson ............. A61N 1/0553 607/117 |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer et al. |
| 2011/0015713 A1 | 1/2011 | Min |
| 2011/0034983 A1 | 2/2011 | Min |
| 2011/0071599 A1 | 3/2011 | Olsen |

(56) References Cited

U.S. PATENT DOCUMENTS

| | | |
|---|---|---|
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1 | 2/2012 | Olsen |
| 2012/0053664 A1 | 3/2012 | Hegland |
| 2012/0059467 A1 | 3/2012 | Drew |
| 2012/0130461 A1 | 5/2012 | Olsen |
| 2012/0330383 A1 | 12/2012 | Wahlstrand |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0170792 A1 | 6/2015 | Alford |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| JP | 11/086641 | 3/2009 |
| WO | WO95/32673 | 12/1995 |
| WO | WO96/16694 | 6/1996 |
| WO | WO96/28951 | 9/1996 |
| WO | WO97/41923 | 11/1997 |
| WO | WO98/48896 | 11/1998 |
| WO | WO99/10035 | 3/1999 |
| WO | WO99/19020 | 4/1999 |
| WO | WO99/60370 | 11/1999 |
| WO | WO00/27279 | 5/2000 |
| WO | WO01/80940 | 11/2001 |
| WO | WO02/00292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO2004/012809 | 2/2004 |
| WO | WO2004/052448 | 6/2004 |
| WO | WO2004/073040 | 8/2004 |
| WO | WO2005/030322 | 4/2005 |
| WO | WO2005/032654 | 4/2005 |
| WO | WO2005/102444 | 11/2005 |
| WO | WO2005/102445 | 11/2005 |
| WO | WO2005/102447 | 11/2005 |
| WO | WO2006/031317 | 3/2006 |
| WO | WO2005/093685 | 9/2006 |
| WO | WO2006/093686 | 9/2006 |
| WO | WO2005/102446 | 11/2006 |
| WO | WO2006/118640 | 11/2006 |
| WO | WO2006/118641 | 11/2006 |
| WO | WO2007/047966 | 4/2007 |
| WO | WO2007/124273 | 11/2007 |
| WO | WO2007/126657 | 11/2007 |
| WO | WO2007/149757 | 12/2007 |
| WO | WO2008/088568 | 7/2008 |
| WO | WO2008/100839 | 8/2008 |
| WO | WO2008/100840 | 8/2008 |
| WO | WO2008/111986 | 9/2008 |
| WO | WO2008/130409 | 10/2008 |
| WO | WO2008/134196 | 11/2008 |
| WO | WO2008/140376 | 11/2008 |
| WO | WO2009/011440 | 9/2009 |
| WO | WO2009/134901 | 11/2009 |
| WO | WO2010/062988 | 7/2010 |
| WO | WO2010/125949 | 11/2010 |
| WO | WO2010/126871 | 11/2010 |
| WO | WO2010/126877 | 11/2010 |
| WO | WO2010/126884 | 11/2010 |
| WO | WO2010/126887 | 11/2010 |
| WO | WO2010/126935 | 11/2010 |
| WO | WO2010/126939 | 11/2010 |
| WO | WO2010/126943 | 11/2010 |
| WO | WO2010/126946 | 11/2010 |
| WO | WO2010/126975 | 11/2010 |
| WO | WO2010/135440 | 11/2010 |
| WO | WO2011/019416 | 2/2011 |
| WO | WO2012/103419 | 8/2012 |
| WO | WO2013/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama.net www.epanorama.net/documents/groundloop/basics.html 28052.00 U.S. Appl. No. 11/739,787.
Finelli, D., et al., "MRI Imaging-Related Heating of Deep Brain Stimulation Electrodes: In Vitro Study", AJNR AM. J. Neuroadiol 23:1, Nov./Dec. 2002.

(56) References Cited

OTHER PUBLICATIONS

Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure, Medtronic, Inc, 2001.

Medtronic Neurostimulation Systems Brochure, Medtronic, Inc., 2002.

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

\* cited by examiner

PAIRED MEDICAL LEAD BODIES WITH BRAIDED CONDUCTIVE SHIELDS HAVING DIFFERENT PHYSICAL PARAMETER VALUES

TECHNICAL FIELD

Embodiments relate to medical leads that have braided conductive shields. More particularly, embodiments relate to medical lead bodies with braided conductive shields where the medical lead bodies are paired and where the braided conductive shields have different physical parameter values.

BACKGROUND

Medical leads provide electrical stimulation from a medical device to a target site within a body of a patient. The medical device is typically implanted or otherwise installed on the body in an accessible area at some distance from the target site, and the medical lead is routed to the target site either through a percutaneous procedure or by surgical implantation depending upon the type and size of the medical lead being implanted.

An issue occurs when the patient is subjected to radiofrequency (RF) electromagnetic energy in excess of the ambient, such as when having a magnetic resonance imaging (MRI) scan. The metal filars within the lead have current induced by the RIP energy. This induced current can produce heating within the medical lead and at the electrodes which can cause harm to the patient. A shield may be included within the lead to limit the amount of current induced on the filars and thereby reduce heating at the electrodes.

In some cases, multiple lead bodies may be paired. For instance, the multiple lead bodies may be positioned adjacently when implanted. One particular example of such positioning is for surgical leads that utilize two lead bodies to carry stimulation signals to a distal paddle. Both lead bodies may include identical braided conductive shields to limit the amount of heating. While the amount of heating at the electrodes may be reduced by the presence of the identical braided conductive shields, it may be desirable to reduce the amount of heating by an even greater amount to allow for even greater scan power levels.

SUMMARY

Embodiments address issues such as these and others by providing paired lead bodies with braided conductive shields having different physical parameter values. The different physical parameter values for the paired leads result in an increased reduction of heating at the electrodes relative to identical braided conductive shields. The physical parameter may be one of a variety of different physical characteristics such as the weave density, weave angle, number of braid wires, braid diameter, and/or braid wire conductivity. The lead bodies may be paired by being aligned adjacently and in close proximity for at least a portion of their length, where this may be achieved through in various manners such as by positioning during implantation and/or by bonding of the lead bodies.

Embodiments provide a medical lead that includes a first lead body housing a first filar connected to a first proximal contact on the first lead body. The first lead body has a first braided conductive shield with a first value for a first physical parameter. The medical lead includes a second lead body housing a second filar connected to a second proximal contact on the second lead body, the second lead body having a second braided conductive shield with a second value for the first physical parameter that is different from the first value. The medical lead also includes a body housing a plurality of electrodes, the body being coupled to the distal end of the first and second lead bodies with a first electrode of the plurality connected to the first filar and a second electrode of the plurality connected to the second filar.

Embodiments provide a medical system that includes a first lead body housing a first filar connected to a first proximal contact on the first lead body. The first lead body has a first braided conductive shield with a first value of a first physical parameter, and the first lead body has a first electrode connected to the first filar. The medical system includes a second lead body housing a second filar connected to a second proximal contact on the second lead body. The second lead body has a second braided conductive shield with a second value of the first physical parameter that is different than the first value, and the second lead body has a second electrode connected to the second filar. The second lead body is positioned adjacently to the first lead body.

Embodiments provide a method of implanting a medical system that involves providing a first lead body housing a first filar connected to a first proximal contact on the first lead body. The first lead body has a first braided conductive shield with a first value of a first physical parameter. The method further involves providing a second lead body housing a second filar connected to a second proximal contact on the second lead body. The second lead body has a second braided conductive shield with a second value of the first physical parameter that is different than the first value. A body houses a plurality of electrodes and the body is coupled to the distal end of the first and second lead bodies with a first electrode of the plurality connected to the first filar and a second electrode of the plurality connected to the second filar. The method further involves implanting the first lead body and the second lead body such that the second lead body is positioned immediately adjacent to the first lead body.

Embodiments provide a method of implanting a medical system that involves providing a first lead body housing a first filar connected to a first proximal contact on the first lead body. The first lead body has a first braided conductive shield with a first value of a first physical parameter, and the first lead body has a first electrode connected to the first filar. The method further involves providing a second lead body housing a second filar connected to a second proximal contact on the second lead body. The second lead body has a second braided conductive shield with a second value of the first physical parameter that is different than the first value, and the second lead body has a second electrode connected to the second filar, The method further involves implanting the first lead body and the second lead body such that the second lead body is positioned immediately adjacent to the first lead body.

DETAILED DESCRIPTION

Embodiments provide paired medical lead bodies that have braided conductive shields with different physical parameter values. This difference in the braided conductive shields results in reduced heating at the electrodes associated with the paired medical lead bodies. The medical lead bodies may be paired by extending to a same paddle attached to the distal ends of both lead bodies. The medical lead bodies may also be paired by being positioned during implantation immediately adjacent to one another without the distal ends necessarily being connected to a same paddle.

The pairing of the lead bodies may also be accomplished by creating a bond between the lead bodies such as by gluing or melting the lead bodies together or by surrounding both lead bodies with tubing such as a heat shrink layer or an additional outer jacket. Such bonding provides the advantages of not requiring the surgeon to properly position the lead bodies to create the pairing and also by improving the predictability of the performance of the pairing.

Figure 1:
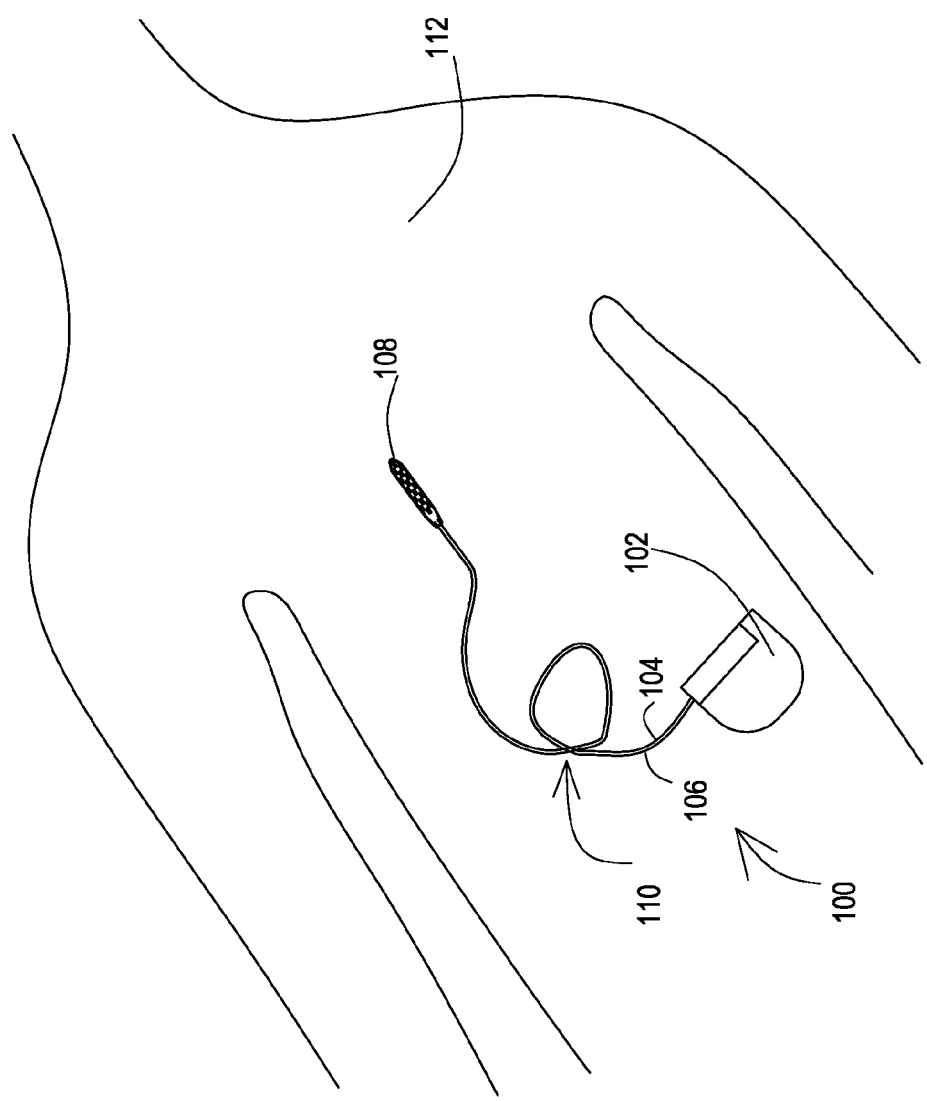
FIG. 1 shows an example of a medical system environment where a medical lead includes paired lead bodies having braided conductive shields with different weave densities.

FIG. 1 shows one example of a medical system 100 that is implanted within a body 112 of a patient. The medical system 100 includes a stimulation device 102 that produces stimulation signals. First and second lead bodies 104, 106 have proximal ends that are coupled to the stimulation device 102. Distal ends of the first and second lead bodies 104, 106 are coupled to a paddle 108 which includes electrodes that deliver the stimulation signals to the body 112.

In this particular example, the first and second lead bodies 104, 106 are implanted such that they remain immediately adjacent to one another from proximal to distal ends. This adjacency allows the braided conductive shields of the first and second lead bodies 104, 106 to electrically couple in the presence of substantial levels of RF energy as might be encountered during an MRI scan. Such an RF coupling of the shields from the adjacency of the lead bodies 104, 106 combined with the physical parameter value differences present between the braided conductive shields reduces the amount of heating that occurs at the electrodes of the paddle 108 during exposure to the RF energy. Without being bound by any particular theory, it is believed that the coupling of the shields where the shields have physical parameter value differences results in destructive interference of the RF waves present on the shields.

In this example, a strain relief loop 110 is also formed by the lead bodies 104, 106. The loop 110 provides slack to reduce strain on the lead bodies 104, 106 during bodily movements by the patient. As shown, the lead bodies 104, 106 maintain their adjacent relationship within the loop 110 and thus retain the RE coupling from the proximal to distal ends that reduces the electrode heating.

Figure 2:
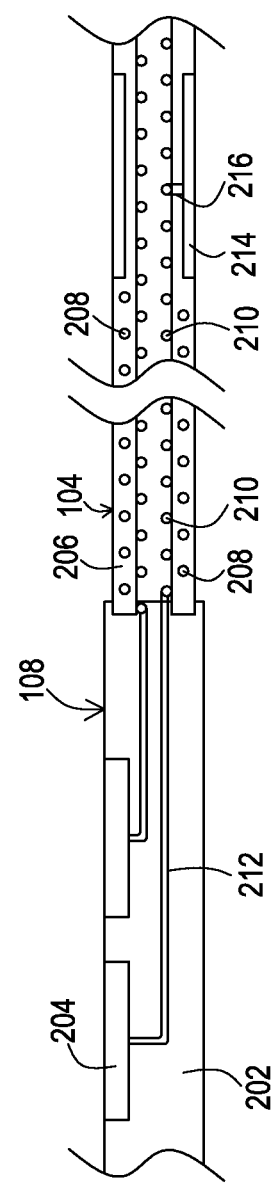
FIG. 2 shows a cross-sectional side view of a medical lead body.

FIG. 2 shows a cross-sectional side view of the paddle 108 and lead body 104 from the medical system 100 of FIG. 1. The paddle 108 is formed by a body 202 that houses a collection of electrodes 204. The body 202 may be constructed in the conventional manner and from conventional paddle materials such as silicone or polyurethane.

The lead body 104 includes a jacket body 206 that extends from the proximal to distal ends. The jacket body 206 provides structural support while protecting the braided shield and conductors from external conditions. The jacket body 206 may be constructed of materials such as silicone or polyurethane.

Shield wires 208 are embedded within the jacket body 206. These shield wires 208 form a braid that ultimately shields conductive filars 210 from the RF energy to reduce the amount of current induced on the filars 210. The shield wires 208 may be constructed of various biocompatible conductors such as tantalum, titanium, MP35 N, platinum, niobium, and the like.

The filars 210 are housed by the tubular body 206 and are surrounded by the shield wires 208. While the filars 210 are shown in a coiled configuration in this cross-sectional view, they may be in other configurations as well such as linear cables. The coiled films 210 are electrically connected via a jumper portion 216 to contacts 214 that are positioned on a proximal end of the lead body 104. The coiled filars 210 are electrically connected via a jumper portion 212 to the electrodes 204 within the body 202 of the paddle 108. The filars may be constructed of biocompatible conductors such as MP35N, titanium molybdenum, platinum, and the like.

While FIG. 2 shows the coupling of the lead body 104 to the paddle body 108, it will be appreciated that the lead body 106 is also coupled to the paddle body 108 in the same manner. Therefore, the discussion with respect to the construction of the lead body 104 and the coupling of the lead body 104 to the body 108 equally apply to the lead body 106.

FIGS. 3-10 show various examples of paired lead bodies 104, 106. The lead bodies 104, 106 of these various examples may be constructed in various manners, such as those discussed above with respect to FIG. 2. Furthermore, in each of these examples, the filars present within the lead bodies 104, 106 may have various configurations, such as being coiled as shown above in FIG. 2 or the filars may be linear.

Figure 3:
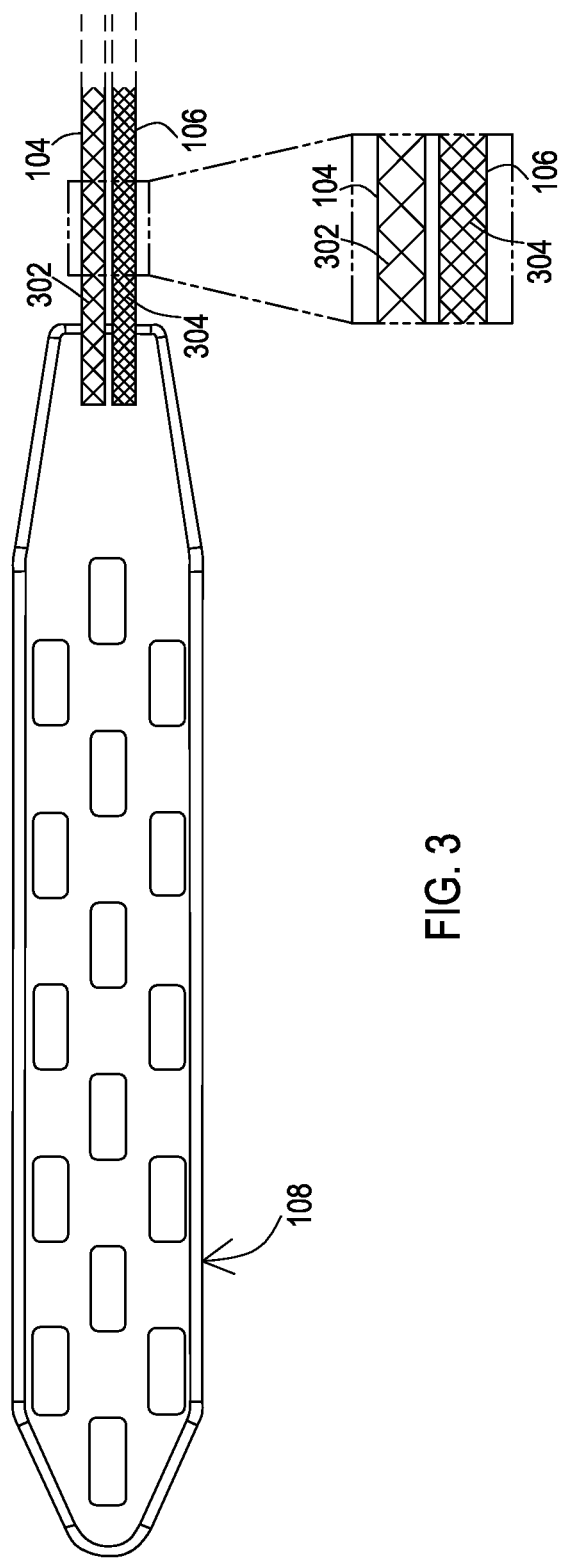
FIG. 3 shows one example of a medical lead having lead bodies with shields that have different numbers of wires and weave densities with even spacing of braid wires.

FIG. 3 shows an example of lead bodies 104, 106 connected to a paddle 108. The lead body 104 includes a braided conductive shield 302, and a lead body 106 that includes a braided conductive shield 304. The braided shield 302 differs from the braided shield 304 by having different values for at least one physical parameter that results in reduced heating at the electrodes of the paddle 108. In this particular example, there are multiple physical parameters that differ, including the number of wires and the weave density, which is the percentage of coverage by the shield material. The weave density difference in this example is provided by a difference in a pie rate, which is the number of braid wire intersections or pics per unit length of the lead body along a given axial line. Here, the braided shield 304 has more braid wires and a higher pic rate than the braided shield 302.

In one specific example, the shield 302 is a 100 pics per inch shield having 8 braid wires, 4 in each direction, while the shield 304 is a 200 pics per inch shield with 16 braid wires, 8 in each direction. In another specific example, the shield 302 is a 75 pics per inch shield while the shield 304 is a 134 pics per inch shield. The particular combination of pic rates between the two shields 302, 304 may be selected based on the combination of all physical characteristics that are present within the lead, including such characteristics as the overall length of the lead bodies 104, 106. Another factor that affects the performance of a given combination of physical parameter values relative to lead bodies having identical shields is the frequency of the RE energy being applied. The optimized combination can be found through empirical studies for a given lead design.

For example, one scenario to consider is a 64 MHz RF field with the electrodes being located approximately 20 cm from the top of the head of the patient, with the center of the MRI coil being 30 cm from the top of the head of the patient. With all else being essentially equal between the lead bodies 104, 106 and the shields 302, 304, it has been found that a 75/134 pics per inch shield combination produces less heating at the electrodes than a 100/200 pics per inch shield combination for 50 cm, 60 cm, and 100 cm lead lengths. However, it has been found that a 100/200 pics per inch shield combination produces less heating at the electrodes than a 75/134 pics per inch shield combination for 80 cm and 90 cm lead lengths.

In other examples where the weave density is different for the braided shields 302, 304, other physical parameters of the braided shields 302, 304 may have the same values or may be different. For instance, both shields 302, 304 may be constructed of the same material such as tantalum wires or may be constructed of different materials such as tantalum wires in one shield and titanium wires in the other.

Figure 4:
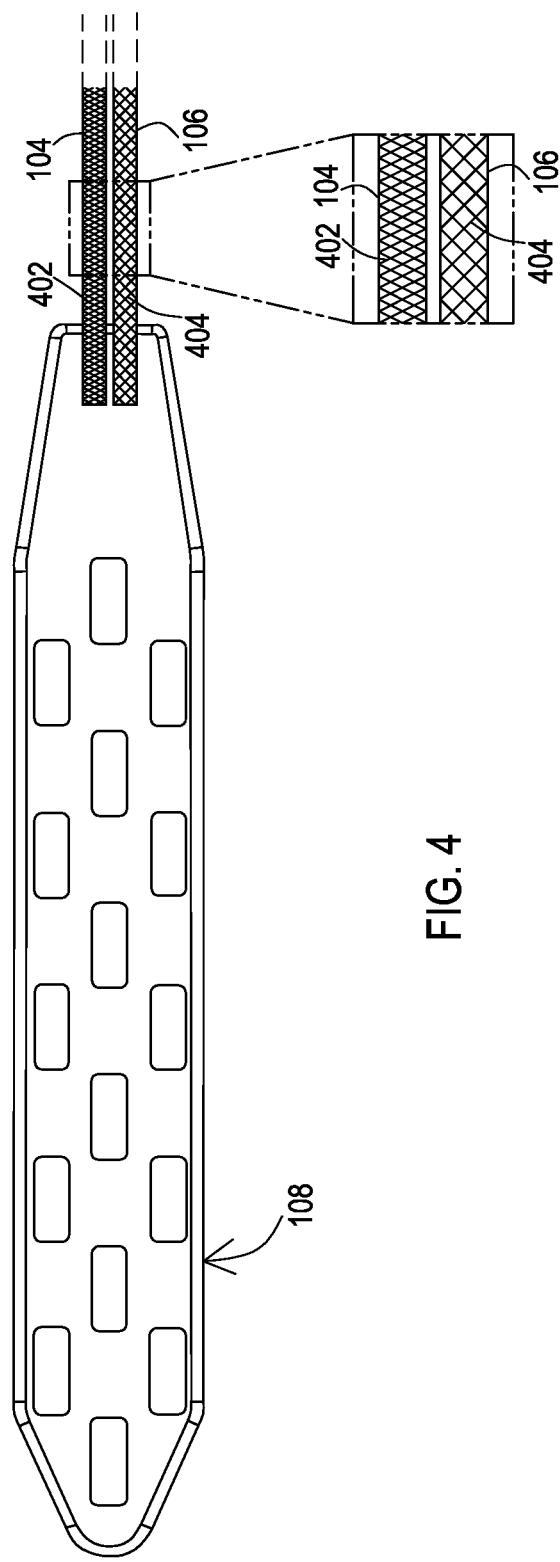
FIG. 4 shows one example of a medical lead having lead bodies with shields that have different weave angles and weave densities.

FIG. 4 shows another example of lead bodies 104, 106 connected to a paddle 108. The lead body 104 includes a braided conductive shield 402, and a lead body 106 that includes a braided conductive shield 404. The braided shield 402 of this example differs from the braided shield 404 by having different values for at least one physical parameter that results in reduced heating at the electrodes of the paddle 108. In this particular example, the physical parameters that differ include the weave angle, which is the angle formed by the braid wires relative to either a longitudinal or lateral dimension of the lead body, and the weave density or pic rate.

In other examples, other physical parameters of the braided shields 402, 404 may have the same values or may be different. For instance, both shields 402, 404 may be constructed of the same material such as tantalum wires or may be constructed of different materials such as tantalum wires in one shield and titanium wires in the other.

Figure 5:
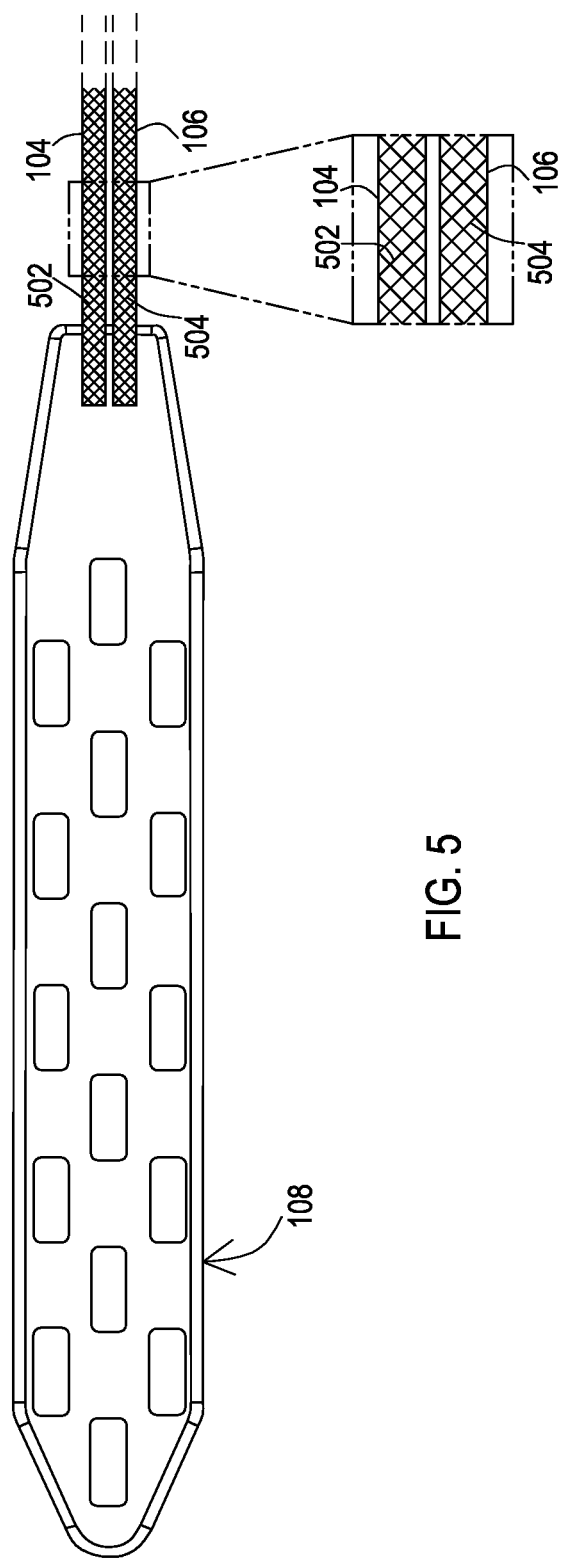
FIG. 5 shows one example of a medical lead having lead bodies with shields that are constructed of braid wire materials with different conductivities.

FIG. 5 shows another example of lead bodies 104, 106 connected to a paddle 108. The lead body 104 includes a braided conductive shield 502, and a lead body 106 that includes a braided conductive shield 504. The braided shield 502 differs from the braided shield 504 by having different values for at least one physical parameter. In this particular example, the physical parameters that differ include the braid material and hence the conductivity of the braid wire. For instance, the shield 502 may be constructed of tantalum while the shield 504 may be constructed of titanium, thereby providing the shields 502, 504 with different values of conductivity.

In other examples where the conductivity differs for the braided shields 502, 504, other physical parameters of the braided shields 502, 504 may have the same values or may be different. For instance, both shields 502, 504 may have the weave density as shown in FIG. 5 or the weave density may be different. Likewise, the weave angle may be the same for both shields 502, 504 as shown in FIG. 5 or may be different. The number of wires used for each of the shields 502, 504 may be the same or may be different. The diameter of the shields 502, 504 may be the same or may be different.

Figure 6:
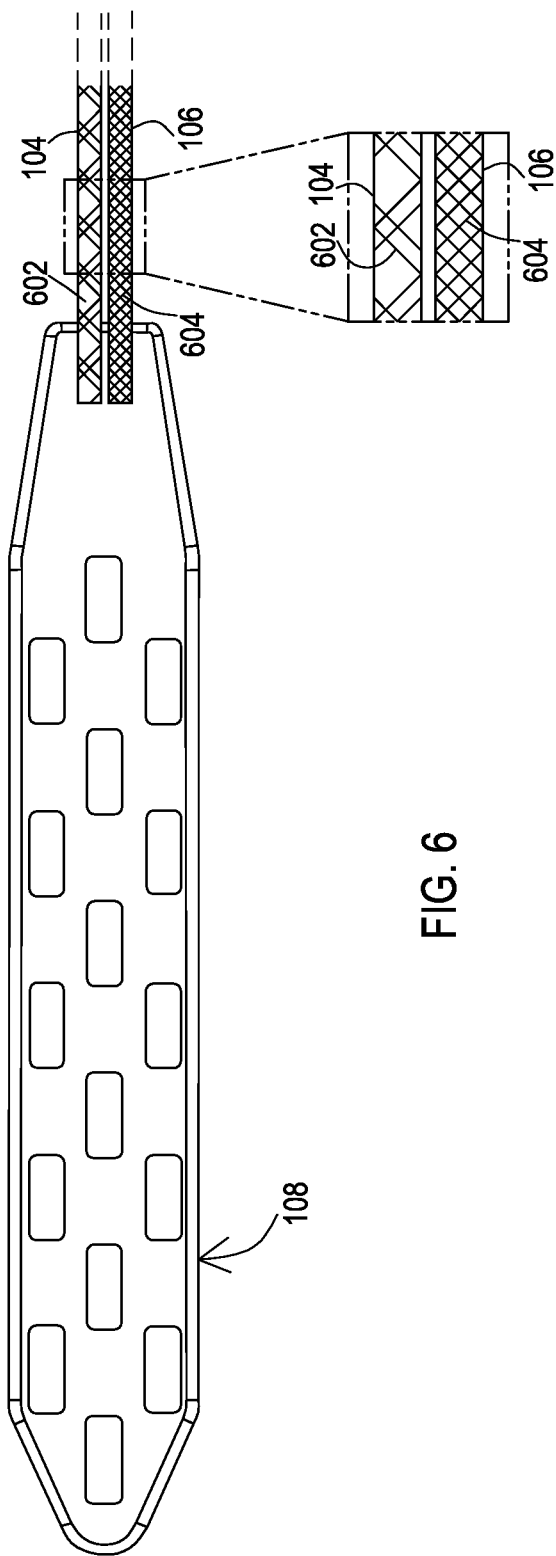
FIG. 6 shows one example of a medical lead having lead bodies with shields that have different numbers of wires and weave densities with uneven spacing of braid wires.

FIG. 6 shows another example of lead bodies 104, 106 connected to a paddle 108. The lead body 104 includes a braided conductive shield 602, and a lead body 106 that includes a braided conductive shield 604. The braided shield 602 differs from the braided shield 604 by having different values for at least one physical parameter. In this particular example, the physical parameters that differ include the number of braid wires that are present where shield 602 has a total of 8 wires with 4 in one direction and 4 in the other. Also, the weave density is lower and in this case the spacing is such that the 4 wires in each direction are grouped into pairs with spacing between pairs being greater than the spacing between each wire of a pair.

Figure 7:
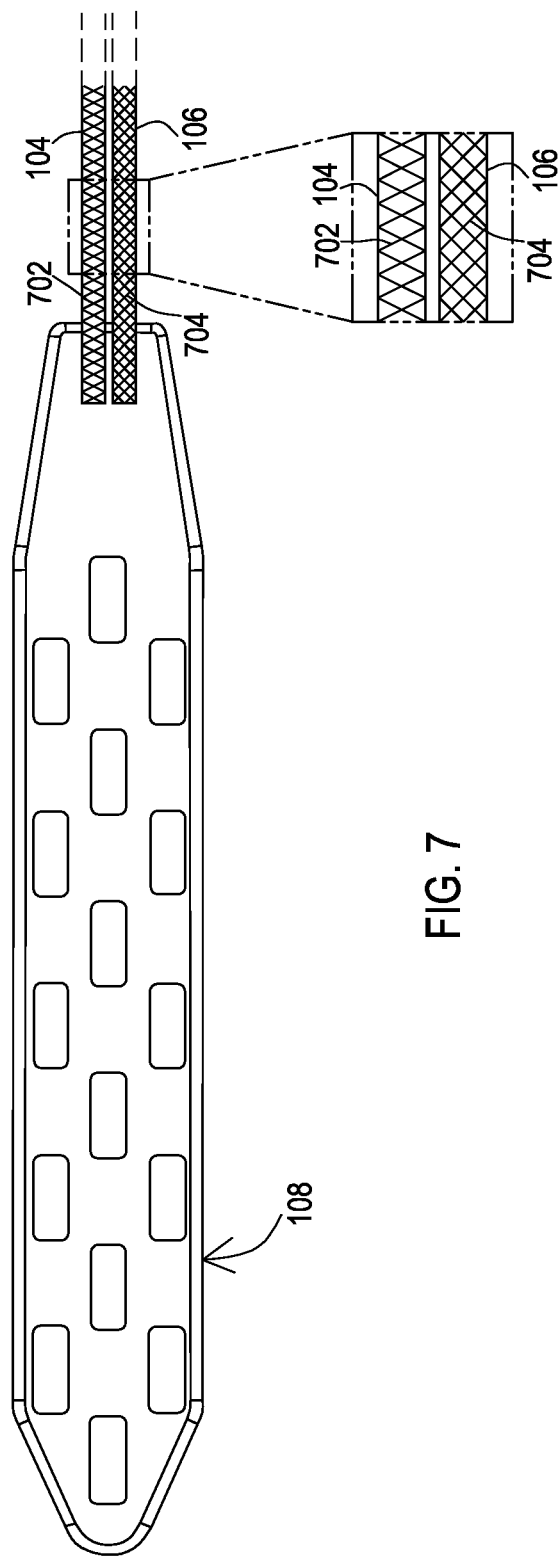
FIG. 7 shows one example of a medical lead having lead bodies with shields that have different numbers of wires and weave angles.

FIG. 7 shows another example of lead bodies 104, 106 connected to a paddle 108. The lead body 104 includes a braided conductive shield 702, and a lead body 106 that includes a braided conductive shield 704. The braided shield 702 differs from the braided shield 704 by having different values for at least one physical parameter. In this particular example, the physical parameters that differ include the number of braid wires that are present where shield 702 has a total of 8 wires with 4 in one direction and 4 in the other. Also, the weave angle relative to the lateral axis is lower.

Figure 8:
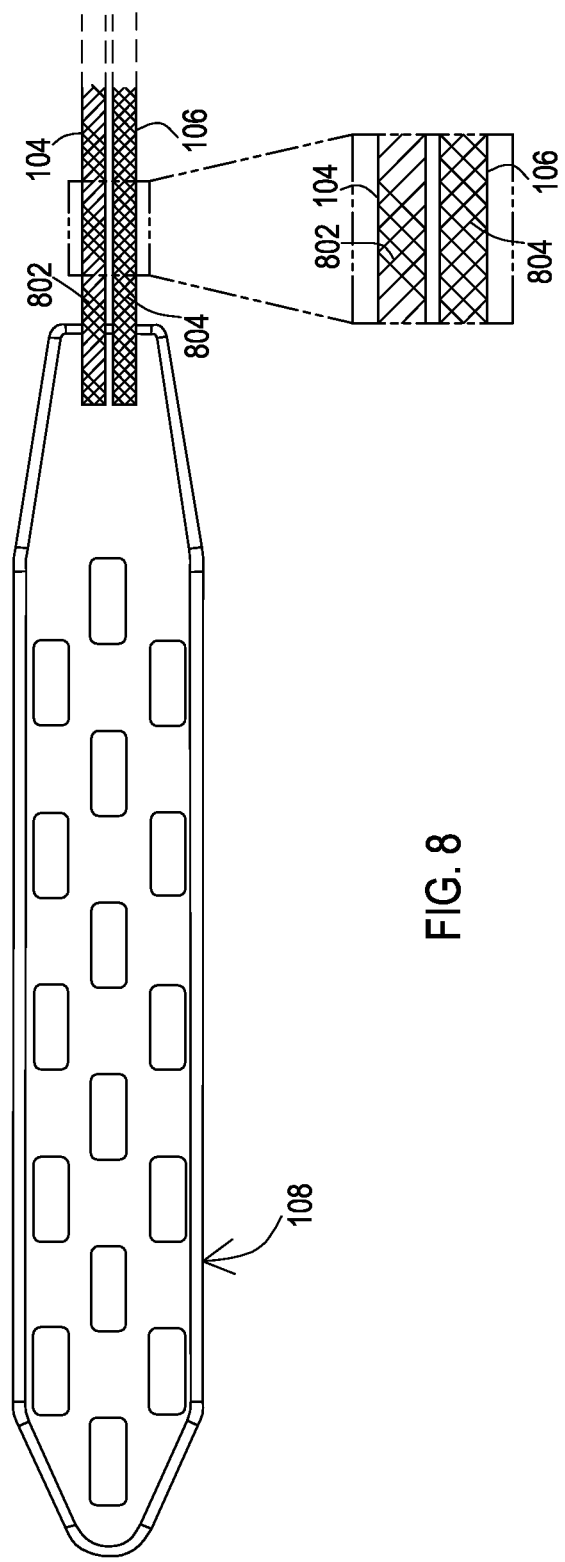
FIG. 8 shows one example of a medical lead having lead bodies with shields that have different numbers of wires where one lead body has an asymmetric wire count and that have different weave densities.

FIG. 8 shows another example of lead bodies 104, 106 connected to a paddle 108. The lead body 104 includes a braided conductive shield 802, and a lead body 106 that includes a braided conductive shield 804. The braided shield 802 differs from the braided shield 804 by having different values for at least one physical parameter. In this particular example, the physical parameters that differ include the number of braid wires that are present where shield 802 has a total of 12 wires with 8 in one direction and 4 in the other. As shown, the spacing between each turn of the group of 4 wires is by a greater amount than the spacing between each wire of the group.

Figure 9:
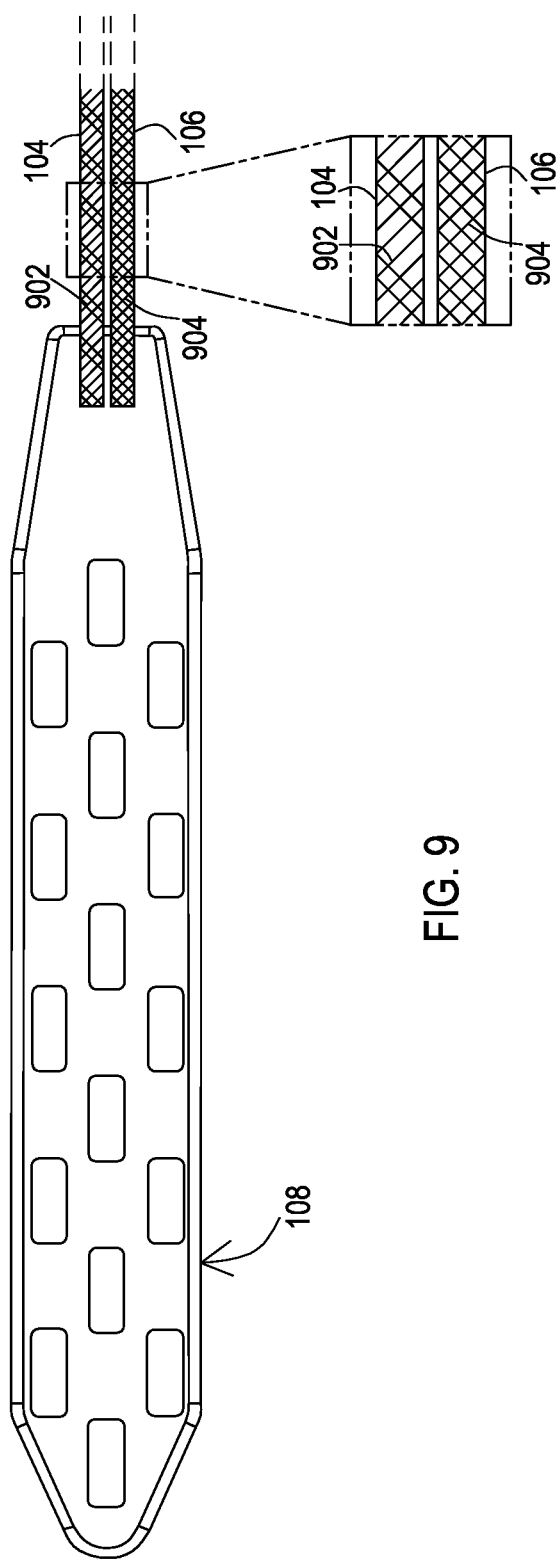
FIG. 9 shows one example of a medical lead having lead bodies with shields that have different numbers of wires where one lead body has an asymmetric wire count and that have different weave densities with uneven spacing of braid wires.

FIG. 9 shows another example of lead bodies 104, 106 connected to a paddle 108. The lead body 104 includes a braided conductive shield 902, and a lead body 106 that includes a braided conductive shield 904. The braided shield 902 differs from the braided shield 904 by having different values for at least one physical parameter. In this particular example, the physical parameters that differ include the number of braid wires that are present where shield 902 has a total of 8 wires with 4 in one direction and 4 in the other. Also, the weave density is lower and in this case the spacing between pairs is greater than the spacing between each wire of a pair.

Figure 10:
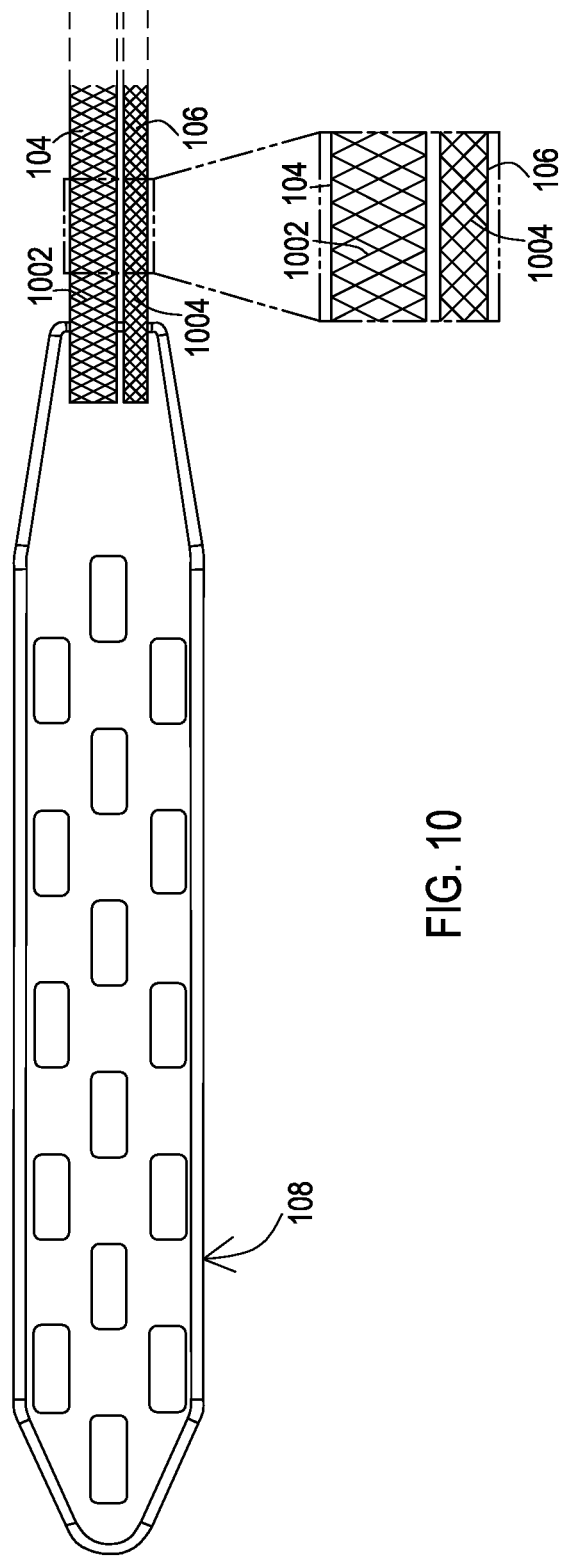
FIG. 10 shows one example of a medical lead having lead bodies with shields that have different diameters and weave angles.

FIG. 10 shows another example of lead bodies 104, 106 connected to a paddle 108. The lead body 104 includes a braided conductive shield 1002, and a lead body 106 that includes a braided conductive shield 1004. The braided shield 1002 differs from the braided shield 1004 by having different values for at least one physical parameter. In this particular example, the physical parameters that differ include diameter of the shield 1002 with a lower weave angle relative to the axial dimension. Also, the weave density is lower and in this case the spacing is uneven by having the 4 wires in each direction grouped into pairs with spacing between pairs being greater than the spacing between the each wire of a pair.

While embodiments have been particularly shown and described, it will be understood by those skilled in the art that various other changes in the form and details may be made therein without departing from the spirit and scope of the invention.

What is claimed is:

1. A method of implanting a medical system, comprising:
    providing a first lead body housing a first filar connected to a first proximal contact on the first lead body, the first lead body having a first braided conductive shield with a first value of a first physical parameter that is independent of a length of the first braided conductive shield, the first lead body having a first electrode connected to the first filar;
    providing a second lead body that is entirely located outside of the first lead body while the first lead body is entirely located outside of the second lead body, the second lead body housing a second filar connected to a second proximal contact on the second lead body, the second lead body having a second braided conductive shield with a second value of the first physical parameter that is different than the first value and that is independent of a length of the first braided conductive shield, the second lead body having a second electrode connected to the second filar; and
    implanting the first lead body and the second lead body such that the second lead body is positioned immediately adjacent to the first lead body.

2. The method of claim 1, wherein a body houses the first and second electrodes, and wherein the distal ends of the first and second lead bodies are coupled to the body.

3. The method of claim 1, further comprising coupling the proximal ends of the first and second lead bodies to a stimulation device.

4. A medical system, comprising:
    a first lead body housing a first filar connected to a first proximal contact on the first lead body, the first lead body having a first braided conductive shield with a first value of a first physical parameter that is independent of a length of the first braided conductive shield, and the first lead body having a first electrode connected to the first filar; and
    a second lead body that is entirely located outside of the first lead body while the first lead body is entirely located outside of the second lead body, the second lead body housing a second filar connected to a second proximal contact on the second lead body, the second lead body having a second braided conductive shield with a second value of the first physical parameter that is different than the first value and that is independent of a length of the second braided conductive shield, the second lead body having a second electrode connected to the second filar, the second lead body being positioned adjacently to the first lead body.

5. The medical system of claim 4, further comprising a body housing the first and second electrodes, and wherein the distal ends of the first and second lead bodies are coupled to the body.

6. The medical system of claim 4, wherein the first physical parameter is weave density.

7. The medical system of claim 6, wherein the first weave density is 100 pics per inch and the second weave density is 200 pics per inch.

8. The medical system of claim 6, wherein the first weave density is 75 pics per inch and the second weave density is 134 pics per inch.

9. The medical system of claim 4, further comprising a stimulation device and wherein the first lead body and the second lead body are coupled to the stimulation device.

10. The medical system of claim 4, wherein the first braided conductive shield comprises tantalum.

11. The medical system of claim 4, wherein the first braided conductive shield is embedded within the first lead body.

12. A medical lead, comprising:
    a first lead body housing a first filar connected to a first proximal contact on the first lead body, the first lead body having a first braided conductive shield with a first value of a first physical parameter that is independent of a length of the first braided conductive shield;
    a second lead body that is entirely located outside of the first lead body while the first lead body is entirely located outside of the second lead body, the second lead body housing a second filar connected to a second proximal contact on the second lead body, the second lead body having a second braided conductive shield with a second value of the first physical parameter that is different than the first value and that is independent of a length of the second braided conductive shield; and
    a body housing a plurality of electrodes, the body being coupled to the distal end of the first and second lead bodies with a first electrode of the plurality connected to the first filar and a second electrode of the plurality connected to the second filar.

13. The medical lead of claim 12, wherein the first physical parameter is weave density.

14. The medical lead of claim 13, wherein the first value of weave density is 100 pics per inch and the second value of weave density is 200 pics per inch.

15. The medical lead of claim 13, wherein the first weave density is 75 pics per inch and the second weave density is 134 pics per inch.

16. The medical lead of claim 12, wherein the first braided conductive shield comprises tantalum.

17. The medical lead of claim 12, wherein the first braided conductive shield is embedded within the first lead body.

18. A method of implanting a medical system, comprising:
    providing a first lead body housing a first filar connected to a first proximal contact on the first lead body, the first lead body having a first braided conductive shield with a first value of a first physical parameter that is independent of a length of the first braided conductive shield;
    providing a second lead body housing a second filar connected to a second proximal contact on the second lead body, the second lead body having a second braided conductive shield with a second value of the first physical parameter that is different than the first value and that is independent of a length of the second braided conductive shield, wherein a body houses a plurality of electrodes, the body being coupled to the distal end of the first and second lead bodies with a first electrode of the plurality connected to the first filar and a second electrode of the plurality connected to the second filar; and implanting the first lead body and the second lead body such that the second lead body is positioned immediately adjacent to the first lead body.

19. The method of claim 18, wherein the first physical parameter is weave density.

20. The method of claim 19, wherein the first weave density is 100 pics per inch and the second weave density is 200 pics per inch.

21. The method of claim 19, wherein the first weave density is 75 pics per inch and the second weave density is 134 pics per inch.

22. The method of claim 18, wherein the first braided conductive shield comprises tantalum.

23. The method of claim 18, wherein the first braided conductive shield is embedded within the first lead body.

24. A method of implanting a medical system, comprising:
providing a first lead body housing a first filar connected to a first proximal contact on the first lead body, the first lead body having a first braided conductive shield with a first value of a first physical parameter, wherein the first physical parameter is weave density;
providing a second lead body housing a second filar connected to a second proximal contact on the second lead body, the second lead body having a second braided conductive shield with a second value of the first physical parameter that is different than the first value, wherein a body houses a plurality of electrodes, the body being coupled to the distal end of the first and second lead bodies with a first electrode of the plurality connected to the first filar and a second electrode of the plurality connected to the second filar; and
implanting the first lead body and the second lead body such that the second lead body is positioned immediately adjacent to the first lead body.

25. A medical lead, comprising:
a first lead body housing a first filar connected to a first proximal contact on the first lead body, the first lead body having a first braided conductive shield with a first value of a first physical parameter, wherein the first physical parameter is weave density;
a second lead body housing a second filar connected to a second proximal contact on the second lead body, the second lead body having a second braided conductive shield with a second value of the first physical parameter that is different than the first value; and
a body housing a plurality of electrodes, the body being coupled to the distal end of the first and second lead bodies with a first electrode of the plurality connected to the first filar and a second electrode of the plurality connected to the second filar.

26. A medical system, comprising:
a first lead body housing a first filar connected to a first proximal contact on the first lead body, the first lead body having a first braided conductive shield with a first value of a first physical parameter, wherein the first physical parameter is weave density, and the first lead body having a first electrode connected to the first filar; and
a second lead body housing a second filar connected to a second proximal contact on the second lead body, the second lead body having a second braided conductive shield with a second value of the first physical parameter that is different than the first value, the second lead body having a second electrode connected to the second filar, the second lead body being positioned adjacently to the first lead body.

* * * * *